(12) United States Patent  (10) Patent No.: US 6,808,903 B1
Pachlatko et al.  (45) Date of Patent: Oct. 26, 2004

(54) PREPARATION OF A MACROCYCLIC LACTONE

(75) Inventors: Johannes Paul Pachlatko, Seltisberg (CH); Thomas Pitterna, Basel (CH); Volker Jungmann, Lörrach (DE)

(73) Assignee: Syngenta Participations AG, Basel (CH)

( * ) Notice: Subject to any disclaimer, the term of this patent is extended or adjusted under 35 U.S.C. 154(b) by 318 days.

(21) Appl. No.: 10/129,853

(22) PCT Filed: Nov. 10, 2000

(86) PCT No.: PCT/EP00/11139

§ 371 (c)(1), (2), (4) Date: May 8, 2002

(87) PCT Pub. No.: WO01/36434

PCT Pub. Date: May 25, 2001

(30) Foreign Application Priority Data

Nov. 12, 1999 (GB) .............................. 9926887

(51) Int. Cl.[7] .............................................. C12P 19/62
(52) U.S. Cl. ...................................................... 435/76
(58) Field of Search .......................................... 435/76

(56) References Cited

U.S. PATENT DOCUMENTS 4,427,663 A 1/1984 Mrozik

FOREIGN PATENT DOCUMENTS

EP 0465121 A 1/1992

Primary Examiner—Herbert J. Lilling
(74) Attorney, Agent, or Firm—Mary Kakefuda

(57) ABSTRACT

Subject of the invention is a process for the preparation of a compound of formula (I) in which $R_1$–$R_9$ represent, independently of each other hydrogen a substituent; m is 0, 1 or 2; n is 0, 1, 2 or 3; and the bonds marked with A, B, C, D, E and F indicate, independently of each other, that two adjacent carbon atoms are connected by a double bond, a single bond, a single bond and an epoxide bridge, or a single bond and a methylene bridge, including, where applicable, an E/Z isomer, a mixture of E/Z isomers, and/or a tautomer thereof, in each case in free form or in salt form, which process comprises I) bringing a compound of formula (II); wherein $R_1$–$R_7$, m, n, A, B, C, D, E and F have the same meanings as given for formula (I) above, into contact with a biocatalyst that is capable of specifically oxidising the alcohol at position 4" in order to form a compound of formula (III), in which $R_1$, $R_2$, $R_3$, $R_4$, $R_5$, $R_6$, $R_7$, m, n, A, B, C, D, E and F have the meanings given for formula (I); and 2) reacting the compound of formula (III) with an amine of the formula $HN(R_8)R_9$, wherein $R_8$ and $R_9$ have the same meanings as given for formula (I), and which is known, in the presence of a reducing agent.

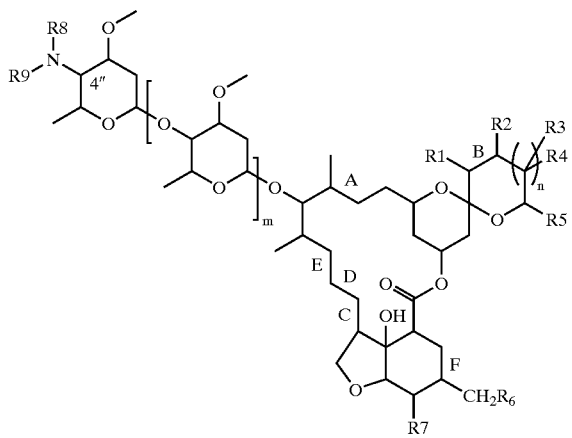

(I)

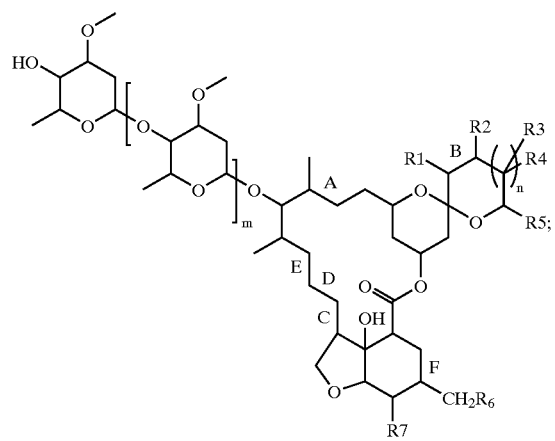

(II)

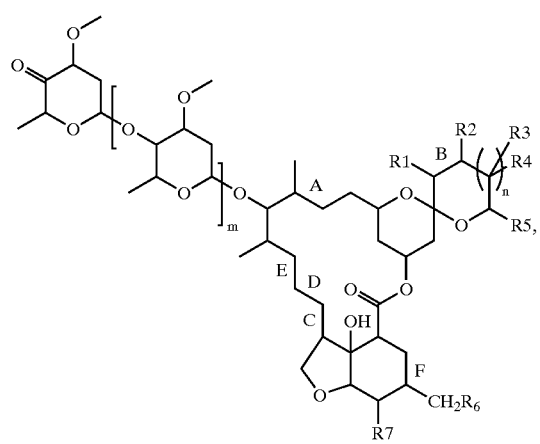

(III)

14 Claims, No Drawings

PREPARATION OF A MACROCYCLIC LACTONE

The present invention relates to a process for the preparation of a macrocyclic lactone, a process for the preparation of the intermediate compounds and the intermediate compounds used in the said process. More particularly the invention relates to a process for the preparation a compound of the formula (I)

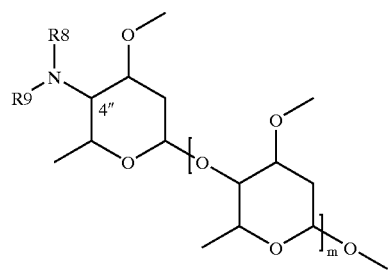

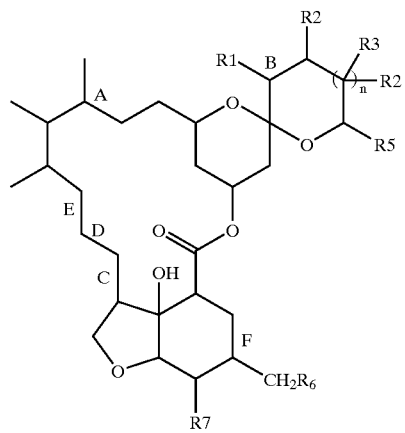

in which $R_1$–$R_9$ represent, independently of each other hydrogen or a substituent, m is 0, 1 or 2;

n is 0, 1, 2 or 3; and the bonds marked with A, B, C, D, E and F indicate, independently of each other, that two adjacent carbon atoms are connected by a double bond, a single bond, a single bond and a epoxide bridge of the formula

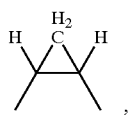

or a single bond and a methylene bridge of the formula

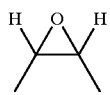

including, where applicable, an E/Z isomer, a mixture of E/Z isomers, and/or a tautomer thereof, in each case in free form or in salt form, which process comprises, 1) bringing a compound of the formula (II)

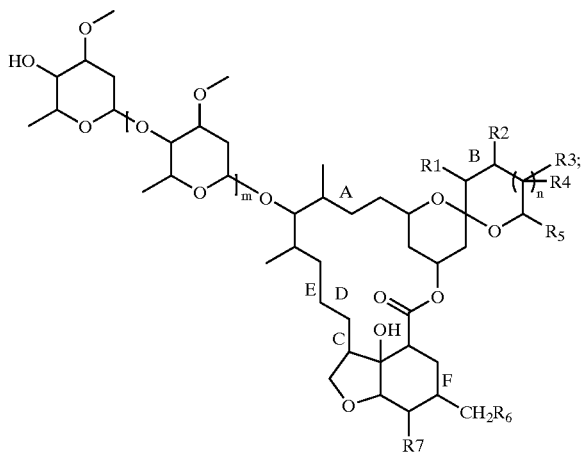

wherein $R_1$–$R_7$, m, n, A, B, C, D, E and F have the same meanings as given for formula (I) above, into contact with a biocatalyst that is capable of specifically oxidising the alcohol at position 4" in order to form a compound of the formula (III)

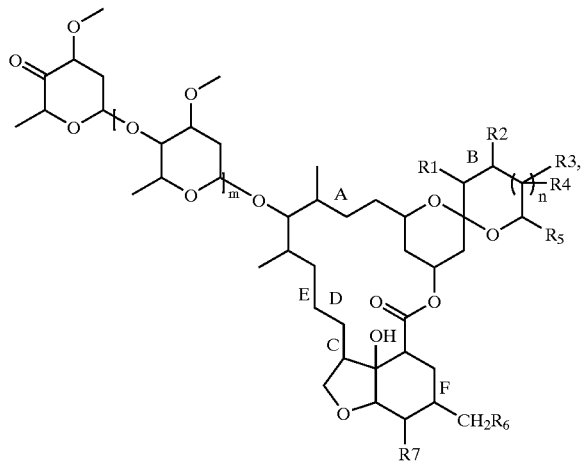

in which $R_1$, $R_2$, $R_3$, $R_4$, $R_5$, $R_6$, $R_7$, m, n, A, B, C, D, E and F have the meanings given for formula (I); and 2) reacting the compound of the formula (II) with an amine of the formula $HN(R_8)R_9$, wherein $R_8$ and $R_9$ have the same meanings as given for formula (I), and which is known, in the presence of a reducing agent; and, in each case, if desired, converting a compound of formula (I) obtainable in accordance with the process or by another method, or an E/Z isomer or tautomer thereof, in each case in free form or in salt form, into a different compound of formula (I) or an E/Z isomer or tautomer thereof, in each case in free form or in salt form, separating a mixture of E/Z isomers obtainable in accordance with the process and isolating the desired isomer, and/or converting a free compound of formula (I) obtainable in accordance with the process or by another method, or an E/Z isomer or tautomer thereof, into a salt or converting a salt, obtainable in accordance with the process or by another method, of a compound of formula (I) or of an E/Z isomer or tautomer thereof into the free compound of formula (I) or an E/Z isomer or tautomer thereof or into a different salt.

Methods of synthesis for the compounds of formula (I) are described in the literature. It has been found, however, that the processes known in the literature cause considerable problems during production basically on account of the low yields and the tedious procedures which have to be used. For example EP-A 0 465 121 discloses 4"-Keto- and 4"-amino-4"-deoxy avermectin compounds and substituted amino derivatives thereof. The 4" hydroxy group on the avermectin compounds are oxidized to a ketone group or replaced with a (substituted) amino group. The hydroxy groups at the 5 and 23-positions need to be protected in order to avoid unwanted oxidations. The 4"-keto compound is aminated to provide the compound corresponding to that of formula (I) above. Accordingly, the known processes are not satisfactory in that respect, giving rise to the need to make available improved preparation processes for those compounds.

The compounds (I), (II) and (III) may be in the form of tautomers. Accordingly, herein-before and hereinafter, where appropriate the compounds (I), (II) and (III) are to be understood to include corresponding tautomers, even if the latter are not specifically mentioned in each case.

The compounds (I), (II) and (III) are capable of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic adds, such as unsubstituted or substituted, for example halo-substituted, $C_1$–$C_4$alkane- or aryl-sulfonic acids, for example methane- or p-toluene-sulfonic acid. Furthermore, compounds of formula (I), (II) and (III) having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or tri-hydroxy-lower alkylamine, for example mono-, di- or tri-ethanolamine. In addition, corresponding internal salts may also be formed. Preference is given within the scope of the invention to agrochemically advantageous salts. In view of the close relationship between the compounds of formula (I), (II) and (III) in free form and in the form of their salts, any reference hereinbefore or hereinafter to the free compounds of formula (I), (II) and (III) or to their respective salts is to be understood as including also the corresponding salts or the free compounds of formula (I), (II) and (III), where appropriate and expedient. The same applies in the case of tautomers of compounds of formula (I), (II) and (III) and the salts thereof. The free form is generally preferred in each case.

Preferred within the scope of this invention is a process for the preparation of compounds of the formula (I), in which n is 1;
m is 1;
A is a double bond;
B is single bond or a double bond,
C is a double bond,
D is a single bond,
E is a double bond,
F is a double bond; or a single bond and a epoxy bridge; or a single bond and a methylene bridge;
$R_1$, $R_2$ and $R_3$ are H;
$R_4$ is methyl;
$R_5$ is $C_1$–$C_{10}$-alkyl, $C_3$–$C_8$-cycloalkyl or $C_2$–$C_{10}$-alkenyl;
$R_6$ is H;
$R_7$ is OH;
$R_8$ and $R_9$ are independently of each other H; $C_1$–$C_{10}$-alkyl or $C_1$–$C_{10}$-acyl; or together form —$(CH_2)_q$—; and
q is 4, 5 or 6.

Especially preferred within the scope of this invention is a process for the preparation of a compound of the formula (I) in which n is 1;
m is 1;
A, B, C, E and F are double bonds;
D is a single bond;
$R_1$, $R_2$, and $R_3$ are H;
$R_4$ is methyl;
$R_5$ is s-butyl or isopropyl;
$R_6$ is H;
$R_7$ is OH;
$R_8$ is methyl
$R_9$ is H.

Very especially preferred is a process for the preparation of Emamectin, more particularly the benzoate salt of Emamectin. Emamectin is a mixture of 4"-deoxy-4"-N-methylamino avermectin $B_{1a}/B_{1b}$ and is described in U.S. Pat. No. 4,4874,749 and as MK-244 in Journal of Organic Chemistry, Vol. 59 (1994), 7704–7708. Salts of emamectin that are especially valuable agrochemically are described in U.S. Pat. No. 5,288,710. The compounds of the formula (I) are valuable pesticides, especially for combating insect and representatives of the order Acarina. The pests mentioned include, for example, those that are mentioned on page 5, lines 55 to 58, page 6 and page 7, lines 1 to 21 in European Patent Application EP-A 736,252. The pests mentioned therein are included thereto in the present subject matter of the invention.

The general terms used hereinbefore and hereinafter have the following meanings, unless defined otherwise:

Carbon-containing groups and compounds each contain from 1 up to and including 8, preferably from 1 up to and including 6, especially from 1 up to and including 4, and more especially 1 or 2, carbon atoms.

Alkyl is either straight-chained, i.e. methyl, ethyl, propyl, butyl, pentyl or hexyl, or branched, e.g. isopropyl, isobutyl, sec-butyl, tert-butyl, isopentyl, neopentyl or isohexyl.

Alkeyl, both as a group per se and as a structural element of other groups and compounds, for example haloalkenyl and arylalkenyl, is, in each case taking due account of the number of carbon atoms contained in the group or compound in question, either straight-chained, for example vinyl, 1-methylvinyl, allyl, 1-butenyl or 2-hexenyl, or branched, for example isopropenyl.

$C_3$–$C_8$Cycloalkyl is cyclopropyl, cyclobutyl, cyclopentyl or cyclohexyl, especially cyclohexyl.

Further aspects of the invention are
the compounds of the formula (III) as defined above; or
a process for the preparation of the compound of the formula (III) starting form the compound of the formula (II) according to step 1) above; or a process for the preparation of the compound of the formula (I) starting form the compound of the formula (III) according to step 2) above.

Within the scope of the present invention, the term "biocatalyst" is meant to include:

a) a living microorganism, for example in the form of vegetative cells, resting cells or freeze dried cells, b) the spores of the said microorganism c) a dead microorganism, preferably in a partially disintegrated form, that is to say with the cell wall/cell membrane mechanically or chemically or by spray drying permeabilized, d) crude extracts of the cell contents of the said microorganism, and e) an enzyme that converts the compounds of the formula (II) into compounds of formula (III).

Bacteria and fungi are especially suitable microorganisms for the process according to the invention. Suitable bacteria are especially representatives of Actinomycetes, especially of the genus Streptomyces. Preferred are strains of the genus Streptomyces selected from the group consisting of *Streptomyces tubercidicus; Streptomyces chattanoogensis, Streptomyces lydicus, Streptomyces saraceticus* and *Streptomyces kasugaensis*. The strains Streptomyces R-922 (*Streptomyces tubercidicus*), and especially Streptomyces I-1529 (*Streptomyces tubercidicus*), have proven particularly suitable for the regiospecific oxidation of the hydroxy group at the 4"-position of compounds of the formula (II).

Streptomyces strains Streptomyces I-1529 and Streptomyces R-922, are deposited pursuant to the provisions of the Budapest Treaty in the DSMZ—Deutsche Sammlung von Mikroorganismen und Zellkulturen GmbH, Mascheroder Weg 1 b, D—38124 Braunschweig—Germany, under accession number DSM-13135 and DSM-13136, respectively, on Nov. 5, 1999.

Additional strains have been identified which can be suitably used to perform the regiospecific oxidation according to the invention including, for example, Streptomyces strain MAAG-7027 (*Streptomyces tubercidicus*), Streptomyces strain DSM-40241 (*Streptomyces saraceticus*, also identified as *Streptomyces chattanoogensis*), Streptomyces strain NRRL-2433 (*Streptomyces lydicus* ssp. *lydicus*) and Streptomyces strain A/96-1208710 (*Streptomyces kasugaensis*). All the above strains are closely related to Streptomyces strains Streptomyces I-1529 and Streptomyces R-922, respectively, which can be demonstrated by a 16s rDNA analysis showing identities of between 99.4% and 100%.

The compounds of formula (I) are known to be highly active agents for controlling plant pests. In the known process for the preparation of compounds of the formula (I) as, for example, described in EP 301 806 and also in the microbial process according to the invention, compounds of formula (II) are used as starting materials.

In the known processes, in a first step the compounds of the formula (II) are protected on the oxygen in position 5, then oxidised to the 4"-ketone, followed by conversion to the amine and deprotection of the masked hydroxy group in position 5, thereby employing conventional protecting group technology as described by Greene and Wuts, 1999 (Protective Groups in Organic Synthesis).

The process according to the present invention has the advantage that it comprises only two steps as compared with four of the known processes. It further avoids the use of protecting groups, and is ecologically safer since fewer chemicals have to be used. The compound of formula (III) resulting from the biocatalytic step according to the invention is known, for example from EP 401 029.

In a specific embodiment the process according to the invention may, in detail, be carried out as follows:

In a first step compounds of the formula (III) are prepared. This can be accomplished by directly contacting a compound of formula (II) with a biocatalyst that is capable of specifically oxidizing the alcohol at position 4" to a ketone of formula (III), and maintaining this contact for a period of time that is sufficient for the oxidation reaction to take place.

Most expediently, the process is carried out by using a microorganism as the biocatalyst, which microorganism is capable of carrying out the oxidation reaction according to the invention. Preferably, said microorganism is cultured in a suitable cultivation medium promoting microbial proliferation and under controlled conditions in the presence of a compound of the formula (II), and maintaining the joint incubation of the said microorganism and its substrate for a time sufficient for the oxidation reaction to occur, preferably until from 25% to 99.9%, more preferably from 50% to 99.9% and most preferably from 80 to 99.9% of the added compound of the formula (II) has been converted into compounds of the formula (III).

Alternatively and more preferably, the process is carried out by firstly culturing a microorganism that is capable of carrying out the oxidation reaction according to the invention in a suitable cultivation medium promoting microbial proliferation and under controlled conditions, and then harvesting the biomass of the microorganism by applying suitable methods such as, for example, by filtration or centrifugation. The biomass of the microorganism is then either immediately used as a biocatalyst for the conversion of compounds of formula (II) into compounds of formula (III) or may be stored in the cold either as such or after freeze drying or spray drying before being used in the reaction. Said microorganism, either freshly harvested or stored as described, and a compound of formula (II) are then jointly incubated in a reaction medium which does not favor microbial proliferation for a time sufficient for the oxidation reaction to occur, preferably until from 25% to 99.9%, more preferably from 50% to 99.9% and most preferably from 80 to 99.9% of the added compound of the formula (II), has been converted into compounds of the formula (III).

The reaction product of the formula (III) obtained in this manner may be separated from starting material of the formula (II) without great technical expenditure by means of customary separating methods, for example by fractional crystallisation or by chromatography. Chromatography includes, for example, column chromatography, thick layer chromatography or thin layer chromatography on mineral carrier materials such as silica gel or on organic exchanger resins.

Instead of vegetative cell structures, microbial spores may be used which spores are harvested from microorganisms that are capable of specifically oxidizing the alcohol at position 4" to a ketone of the formula (III), and are then incubated with a compound of the formula (II) for a period of time that is sufficient for the corresponding oxidation reaction to take place. The incubation of spores and substrate is preferably carried out in the absence of culture medium in order to prevent the spores from germinating.

Compounds of the formula (II) are used as a substrate for the oxidation reaction according to the invention. These compounds are known (see DE 2717040) or can be prepared from known compounds analogously to known processes. They are suitable for controlling pests in animals and plants and are furthermore valuable starting materials or intermediates in the preparation of compounds of the formula (I). The preparation of compounds of formula (III) can also be carried out by using for the oxidation of the compounds of formula (II) not the microorganism itself but active constituents originating from this microorganism (according to the definitions b) to a) above) that are capable of specifically oxidizing the alcohol at position 4″ to a ketone of the formula (III).

Accordingly, a further aspect of the present invention is the use in immobilised form of vegetative microorganism cells, cell-free extracts, spores, enzymes and mixtures of enzymes of the said microorganisms that are capable of specifically oxidizing the alcohol at position 4″ to a ketone of the formula (III).

The immobilisation of the said biocatalysts can be carried out analogously to processes known per se. Within the scope of the present invention there may be mentioned especially processes that are based on adsorptive binding or ionic or covalent bonding of the said biocatalysts to solid, as a rule water-insoluble, carrier materials, on crosslinking of biocatalysts by bi- or poly-functional reagents, on matrix encapsulation, on membrane separation or on a combination of two or more of the above-mentioned processes.

The adsorptive binding to water-insoluble carriers (adsorbents) is carried out especially by van der Waals forces. Numerous inorganic and organic compounds and also synthetic polymers are suitable as adsorbents.

Methods for such an immobilisation of microorganisms are described by Bickerstaff (Ed.), 1997 (Immobilisation of Enzymes and Cells), van Haecht et al., 1985 (yeast cells/glass), Black et al., 1984 (yeast cells/refined steel, polyester), Wiegel and Dykstra, 1984 (clostridia/cellulose, hemicellulose), Förberg and Häggström, 1984 (clostridia/wood shavings) and also by Ehrhardt and Rehm, 1985 (Pseudomonads/active carbon). Corresponding details for the use of enzymes immobilised by adsorptive binding are to be found in Krakowiak et al., 1984 (glucoamylase/aluminium oxide), Cabral et al., 1984 (glucoamylase/titanium-activated glass), Miyawaki and Wingard 1984 (glucose oxidase/active carbon), Kato and Horikoshi, 1984 (glucose transferase/synthetic resin) inter alia. Ionic bonds are based on electrostatic attractions between oppositely charged groups of the carrier material (such as, for example, commercially available ion exchangers, for example based on polysaccharides or on synthetic resins) and of the biocatalyst to be bound.

Methods of immobilising microorganisms based on ionic bonding are described by DiLuccio and Kirwan, 1984 (Azotobacter spec./Cellex E (cellulose)) and by Giard et al., 1977 (animal cells/DEAE-Sephadex). A corresponding immobilisation of enzymes can be carried out in accordance with the details given by Angelino et al., 1985 (aldehyde oxidase/octylamino-Sepharose 4B), Hofstee, 1973 (lactate dehydrogenase/octylamino-Sephadex), Kühn et al., 1980 (glucose oxidase/DEAE-Sephadex, DEAE-cellulose) and others.

A further method of immobilisation is based on the use of covalent bonding forces, which generally result in fixed linking of biocatalysts to one another or between biocatalyst and carrier material. Suitable carrier materials are porous materials, such as glasses, silica or other insoluble inorganic materials.

Within the scope of the process according to the invention, the microorganisms can be immobilised, for example, analogously to Messing and Oppermann, 1979 (Enterobacteria/borosilicate glass; yeast cells/zirconium oxide), Romanovskaya et al., 1981 (methane bacteria/Silochrome), Navarro and Durand, 1977 (yeast cells/porous silica).

The immobilisation of enzymes can be carried out in accordance with the method described by Weetall and Mason, 1973 (papain/porous glass) and Monsan et al., 1984 (invertase/porous silica).

In the process according to the invention not only are the carrier materials already mentioned suitable for immobilisation but also a whole series of natural or synthetic polymers, such as, for example, cellulose, dextran, starch, agarose etc. or polymers, for example based on acrylic and methacrylic acid derivatives, that are usually used in the manufacture of reactive copolymers. Suitable reactive groups by means of which a bond to the biocatalyst is formed are reactive dinitrofluorophenyl or isothiocyanate groups, or especially oxirane and acid anhydride groups. A further possibility resides in the chloride activation of resins carrying carboxy groups, which are commercially available, for example, under the trade names Amberlite® XE-64 and Amberlite® IRC-50.

The immobilisation of microorganisms with the aid of natural or synthetic carrier materials can be carried out as described by Chipley, 1974 (Bacillus subtilis/agarose), Gainer et al., 1980 (Azotobacter species/cellulose), Jack and Zajic, 1977 (Micrococcus/carboxymethylcellulose), Jirku et al., 1980 (yeast cells/hydroxyalkylmethacrylate) and also by Shimizu et al., 1975 (bacterial cells/ethylene-maleic anhydride copolymer). The immobilisation of enzymes can be carried out analogously to Cannon et al., 1984 (lactate oxidase/cellulose), Dennis et al., 1984 (chymotrypsin/Sepharose), Ibrahim et al., 1985 (epoxy hydrolase/dextran); Beddows et al., 1981 (α-galactosidase/nylon-acrylate copolymer), Raghunath et al., 1984 (urease/methacrylate-acrylate), inter alia.

In the crosslinking process, the biocatalysts are bonded to each other by bi- or poly-functional reagents, such as glutardialdehyde, diisocyanates inter alia and form characteristically insoluble, usually gelatinous aggregates of high molecular weight.

Such immobilisations of microorganisms can be carried out analogously to De Rosa et al., 1981 (bacterial cells/co-crosslinking with eggalbumin by means of glutardialdehyde). Processes for the immobilisation of enzymes that can be used within the scope of the present invention are described by Barbaric et al., 1984 (invertase/crosslinking with adipic acid dihydrazide), Talsky and Gianitsopoulos, 1984 (chymotrypsin/peptide bond between the enzyme molecules without crosslinking agent), Workman and Day, 1984 (inulinase/crosslinking of the enzyme-containing cells with glutardialdehyde), Khan and Siddiqi, 1985 (pepsin/crosslinking with glutardialdehyde), Bachmann et al., 1981 (glucose isomerase/co-crosslinking with gelatine by means of glutardialdehyde), Kaul et al., 1984 (α-galactosidase/co-crosslinking with egg albumin by means of glutardialdehyde).

Matrix encapsulation comprises the inclusion of the biocatalysts in natural or synthetic polymers, which are usually of gelatinous structure. Matrix materials that are especially suitable for the inclusion of cells, organelles and spores are natural polymers such as alginate, carrageenan, pectin, agar, agarose or gelatine, since these compounds are non-toxic and protect the cells during handling. Also suitable are synthetic polymers, such as, for example, polyacrylamides, photo-crosslinked resins inter alia. The form of the matrix encapsulation is variable within wide limits and may include, for example, spherical, cylindrical, fibrous and sheet forms. The immobilisation of microorganisms with the aid of natural or synthetic matrix materials can be carried out as described by Mazumder et al., 1985 (bacterial cells/ photo-crosslinked resins), Bettmann and Rehm, 1984 (bacterial cells/polyacrylamide hydrazide), Umemura et al., 1984 (bacterial cells/carrageenan), Karube et al., 1985 (bacterial protoplasts/agar-acetylcellulose), Cantarella et al., 1984 (yeast cells/hydroxyethylmethacrylate), Qureshi and Tamhane, 1985 (yeast cells/alginate), Deo and Gaucher, 1984 (Hyphomycetes/carrageenan), Eikmeier and Rehm, 1984 (Hyphomycetes/alginate), Bihari et al., 1984 (Hyphomycetes conidial/polyacrylamide), Vogel and Brodelius, 1984 (plant cells/alginate, agarose), Nakajima et al., 1985 (plant cells/agar, alginate, carrageenan).

The immobilisation of enzymes can be carried out analogously to Mori et al., 1972 (aminoacylase/polyacrylamide).

Membrane separation involves the creation of specific defined areas in which the reaction proceeds. The basic variants of membrane separation are differentiated as follows:

a) microencapsulation
b) liposome technique
c) the use of biocatalyst in membrane reactors.

The above-described immobilisation methods can be combined with one another, such as, for example, adsorption and crosslinking. In that case the enzymes are first of all adsorbed on a carrier and then crosslinked with one another by a bifunctional reagent.

The incubation of the biocatalysts used within the scope of the present invention with compounds of the formula (II) for the specific oxidation of the alcohol at position 4" to a ketone of the formula (III) can be carried out with the aid of processes such as those customary in applied microbiology. In addition to the use of shake cultures there may be mentioned especially various fermenter systems that have long been established in microbiological research and industrial production.

The main task of the bioreactors is the creation of optimum hydrodynamic conditions in order to reduce the apparent Michaelis constants and to increase the reaction speed.

This is essentially achieved by maintaining an adequate relative movement between biocatalyst and surrounding medium, which increases the external mass transfer to such an extent that its hindrance in practice no longer applies.

Types of reactors that are suitable for the process concerned include, for example, stirred vessel reactors, loop-type reactors, bed reactors, fluidised bed reactors, membrane reactors and also numerous special forms of reactor, for example sieve-stirred reactors, rhomboid reactors, tube reactors inter alia (W. Hartmeier, Immobilisierte Biokatalysatoren, 1986; W. Crueger and A. Crueger, Biotechnologie-Lehrbuch der angewandten Mikrobiologie, 1984; P. Präve et al., Handbuch der Biotechnologie, 1984). The use of stirred vessel reactors is preferred within the scope of the present invention.

Stirred vessel reactors are among the types of reactor most used in the biotechnological art of fermentation. This type of reactor ensures a rapid and thorough mixing of substrate and biocatalyst as a result of high stirring capacities and a high oxygen transfer capacity.

The advantages of stirred vessel reactors reside in their simple and thus economical construction and in their well-researched properties.

In principle, when using stirred vessel reactors two kinds of operation are possible: first of all a "batch-type" operated process, the so-called "batch" process, and, secondly, a continuous process.

In the "batch" process the biocatalysts are removed by separation or filtration once the process is complete and are either discarded (vegetative cells) or are used again in a second batch (immobilised biocatalysts).

When using the continuous process, there is a permanent continuous exchange of new substrate for the end product of the reaction. The biocatalysts must be prevented from leaving the reactor by means of suitable measures (sieve, filters, return devices).

The culturing of vegetative microorganism cells within the scope of the present invention is carried out according to known generally customary methods, liquid nutrient media preferably being used for reasons of practicability.

The composition of the nutrient media varies depending on the microorganism used. Generally, complex media with poorly defined, readily assimilable carbon(C) and nitrogen (N) sources are preferred, as customarily used, for example, also for the production of antibiotics.

In addition, vitamins and essential metal ions are necessary which, however, are as a rule contained in an adequate concentration as constituents or impurities in the complex nutrient media used. If desired, the said constituents such as, for example, essential vitamins and also $Na^+$, $K^+$, $Ca^{2+}$, $Mg^{2+}$, $NH_4^+$, $(SO_4)2-$, $Cl^-$, $(CO_3)^{2-}$ ions and the trace elements cobalt and manganese and zinc, inter alia, may be added in the form of their salts. Especially suitable nitrogen sources apart from yeast extracts, yeast hydrolysates, yeast autolysates and yeast cells are especially soya meal, maize meal, oat meal, edamine (enzymatically digested lactalbumin), peptone, casein hydrolysate, corn steep liquors and meat extracts.

The preferred concentration of the said N-sources is from 0.1 to 6 g/l. Suitable carbon sources are, especially, glucose, lactose, sucrose, dextrose, maltose, starch, cerelose, cellulose, mannitol, malt extract, and molasses. The preferred concentration range of said carbon sources is from 1.0 to 25 g/l. The use of D-glucose, soluble starch or malt extract and also of cerelose as carbon source is of advantage for the oxidation process described in the following, especially if the microorganisms used are representatives of the genus Streptomyces. Thus, for example, the following culture media are excellently suitable for representatives of the genus Streptomyces:

Medium 1

1.0 g of soluble starch
0.2 g of peptone
0.2 g of yeast extract
adjust to 1 liter with distilled water, adjust to pH 7 with NaOH, autoclave.

Medium 2

4.0 g of D-glucose
10.0 g of malt extract
4.0 g of yeast extract
adjust to 1 liter with distilled water, adjust to pH 7 with NaOH, autoclave.

Medium 3

10.0 g of glycerol
20.0 g of dextrin
10.0 g of soytone (Difco Manual, 9th ed., Detroit, Difco Laboratories, 1969)
2.0 g of $(NH_4)_2SO_4$
2.0 g of $CaCO_3$
adjust to 1 liter with distilled water, adjust to pH 7 with NaOH, autoclave.

Medium 4

10.0 g of D-glucose
10.0 g of malt extract 3.0 g of yeast extract
10.0 g of Pharmamedia (Traders Protein, Southern Cotton Oil Co., Memphis Tenn., USA)
1.0 g of meat extract
adjust to 1 liter with distilled water, adjust to pH 7 with NaOH, autoclave.

Medium 5 (ISP-2 Agar)

| | |
|---|---|
| yeast extract | 4 g (Oxoid Ltd, Basingstoke, Hampshire, England) |
| D(+)-glucose | 4 g |
| bacto malt extract | 10 g (Difco No. 0186-17-7) |
| agar | 20 g (Difco No. 0140-01) | are dissolved in 1 l of demineralized water, and the pH is adjusted to 7.0. The solution is sterilized at 121° C. for 20 min, cooled down and kept at 55° C. for the short time needed for the immediate preparation of the agar plates.

Medium 6 (PHG Medium)

| | |
|---|---|
| peptone | 10 g (Sigma 0521) |
| yeast extract | 10 g (Difco) |
| D-(+)-glucose | 10 g |
| NaCl | 2 g |
| $MgSO_4 \times 7H_2O$ | 0.15 g |
| $NaH_2PO_4 \times H_2O$ | 1.3 g |
| $K_2HPO_4$ | 4.4 g | are dissolved in 1 l of demineralized water, and the pH is adjusted to 7.0.

The above-mentioned media are also excellently suitable for culturing representatives of the genus Streptomyces and for carrying out the oxidation reaction. Both the above general data about the composition of the media, and also the media listed in detail herein, serve merely to illustrate the present invention and are not of a limiting nature.

Apart from the composition of the media, the procedure used to produce the media, such as, for example, the dissolving or suspending sequence, the sterilisation of the nutrient solution as a whole or the sterilisation of the individual constituents, the prevention of contamination inter alia, also plays a significant role and should be optimised accordingly for the production process concerned.

It should also be noted that the sterilisation may cause alterations in the pH value of the nutrient medium and also precipitations.

The remaining culturing methods also correspond to the processes customarily used for culturing microorganisms.

On a small scale, the fermentations carried out within the scope of the present invention, including any precultures, are usually in the form of shake cultures, in which case it is advantageous to use glass flasks of from 0.1 to 5 liters, preferably from 0.5 to 5 liters capacity, which contain from 0.05 to 2 liters, preferably from 0.1 to 2 liters of nutrient medium. The flasks are preferably equipped with a baffle. After autoclaving and adjusting the pH to values of from pH 4 to pH 8, especially from pH 7.0 to pH 7.5 (bacteria) or to values of from pH 6 to pH 7.5 (fungi), the flasks are inoculated with the corresponding microorganism cultures under sterile conditions. The inoculation material used is generally a preculture that has been produced from preserved inoculation material in accordance with the data given below.

The cultures, including any precultures, are advantageously grown under aerobic conditions at a temperature of from about 25° C. to about 37° C., preferably about 26° C. to about 30° C., but especially at about 28° C., with continuous shaking at between about 80 rpm to about 300 rpm, preferably between about 100 rpm and 250 rpm, but especially at about 120 rpm (revolutions per minute) on a rotatory shaking machine. Under the above-mentioned conditions, with Streptomyces an optimum oxidation activity has generally been reached after from 1.5 to 7 days' culturing.

Once the catalytic capacity of the cells is sufficiently high to carry out the desired oxidation reaction, preferably after 40 hours, the substrate (compounds of the formula (II)) is added, whereby the microorganisms and the substance to be oxidized can be brought into contact with one another in any manner. For practical reasons, it has proved advantageous to add the substrate, that is to say a compound of the formula (II), to the microorganism in nutrient solution.

The substance to be oxidized can be used, for example, in powder form or in the form of a solution either in a suitable solvent such as, for example, dimethylformamide, acetone, dimethyl sulfoxide, N-methyl-2-pyrrolidone or an alcoholic solvent such as, for example, methanol, ethanol, isopropanol or tert.-butanol, or an ether solvent such as, for example, tetrahydrofuran or 1,4-dioxane (0.5 to 15% by volume, preferably 2% by volume) or an ester solvent such as, for example, ethyl acetate or a hydrocarbon solvent such as, for example, octane or cyclohexane or toluene or xylene, or in an a mixture of a suitable solvent and a suitable surfactant. The term "surfactant" comprises ionic, non-ionic and zwitterionic surfactants and will also be understood to include mixtures of surfactants.

Both water-soluble soaps and water-soluble synthetic surface-active compounds are suitable anionic surfactants. Suitable soaps are the alkali metal salts, alkaline earth metal salts or unsubstituted or substituted ammonium salts of higher fatty adds ($C_{10}$–$C_{22}$), e.g. the sodium or potassium salts of oleic or stearic acid, or of natural fatty acid mixtures which can be obtained, e.g., from coconut oil or tallow oil. Further suitable surfactants are also the fatty acid methyl-taurin salts. More frequently, however, so-called synthetic surfactants are used, especially fatty sulfonates, fatty sulfates, sulfonated benz-imidazole derivatives or alkylarylsulfonates. The fatty sulfonates or sulfates are usually in the form of alkali metal salts, alkaline earth metal salts or unsubstituted or substituted ammonium salts and contain a $C_{10}$–$C_{22}$-alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and form-aldehyde. Also suitable anionic surfactants are bile acid salts, e.g. the sodium salts of cholic acid or deoxycholic acid. Also suitable are corresponding phosphates, e.g. salts of the phosphoric acid ester of an adduct of p-nonylphenol with 4 to 14 moles of ethylene oxide; or phospholipids.

Suitable cationic surfactants are tetraalkyl ammonium salts, e.g. cetyl trimethylammonium bromide Suitable neutral surfactants are alkyl glycosides, e.g alkyl-β-D glucopyranosides, alkyl-β-D thioglucopyranosides, alkyl-β-D maltosides containing a $C_6$–$C_{12}$-alkyl radical. Further suitable neutral surfactants are glucamides, e.g.

N,N-bis(3-D-Gluconamidopropyl)-cholamide, N,N-bis(3-D-Gluconamidopropyl)-deoxycholamide, fatty acid N-methylglucamides containing a $C_7$–$C_{12}$-acyl radical. Further suitable neutral surfactants are mono- and polydisperse polyoxyethylenes, e.g. BRIJ®, GENAPOL®, LUBROL®, PLURONIC®, THESIT®, TRITON®, TWEEN®.

Suitable zwitterionic surfactants are N,N,N-trialkyl glycines, e.g. N-n-dodecyl-N,N,-dimethylglycine. Further suitable zwitterionic surfactants are ω-N,N,N-trialkylammonium alkyl sulfonates, e.g. 3-(N-alkyl-N,N-dimethyl)-1-propane-sulfonate containing a $C_8$–$C_{16}$-alkyl radical. Further suitable zwitterionic surfactants are 3-[(3-cholamidopropyl)-dimethylammonio]-1-propane-sulfonate and 3-[(3-cholamidopropyl)-dimethylammonio]-2-hydroxy-1-propane-sulfonate.

The surfactants customarily employed in the art of solubilisation and formulation are described, inter alia, in the following publications: Bhairi S. M. (1997) "A guide to the Properties and Uses of Detergents in Biology and Biochemistry", Calblochem-Novabiochem Corp., San Diego Calif.; "1999 International McCutcheon's Emulsifiers and Detergents" The Manufacturing Confectioner Publishing Co., Glen Rock, N.J., U.S.A.

The course of the reaction is continuously monitored by chromatographic methods generally used in microbiological research.

The present invention also relates to the culturing of microorganisms that are capable of specifically oxidizing the alcohol at position 4" to a ketone of the formula (III), and to the incubation thereof with the said compounds in bioreactors, especially in bioreactors of the stirred vessel reactor type. In order to ensure an optimum rate of product formation in the actual production fermenter, it is recommended that the microorganisms first of all be multiplied in precultures. The number of fermenter precultures depends on the inoculation material concentration that is optimum in each particular case. Advantageously, depending on the microorganisms used, the following concentrations of inoculation material are produced for a fermenter stage: bacteria 0.1–3%, fungi 5–10%, Actinomycetales 5–10%.

The inoculation of small fermenters (up to 20 L) is usually carried out using shaken flask precultures. In this case the total flask content is used to inoculate the fermenter. The starting material used for the production of precultures is usually preserved inoculation material which may be, for example, in the form of lyophilisates, or of frozen or cold-stored material. The preserved inoculation material used within the scope of the present invention is preferably material stored at –80° C.

Multiplying the inoculation material is preferably carried out in liquid media in glass flasks on a rotatory shaking machine or, when using spores, on solid nutrient substrates. The conditions relating to nutrient substrates and culturing parameters, such as temperature, pH, introduction of oxygen inter alia, must be optimised in accordance with the microorganism or process used. The growth times for the preserved inoculation material vary from a few hours to several days depending on the starting material used.

| lyophilisates frozen preserved | 3–10 days |
|---|---|
| bacteria | 4–18 hours |
| Actinomycetales | 1–5 days |
| fungi | 1–7 days |

| -continued | |
|---|---|
| cold-stored cultures | |
| bacteria | 4–24 hours |
| Actinomycetales | 1–3 days |
| fungi | 15 days |

If spores are used as inoculation material, the spores are first of all multiplied from preserved inoculation material on solid nutrient substrates under standardised conditions (sterile aeration, climatic chamber). If porous nutrient substrates based on peat, bran, rice or barley are used, the cultures are shaken thoroughly daily to achieve high spore densities. A further possibility lies in culturing the preserved inoculation material on nutrient media solidified by agar or other customary gelling agents, it being preferable to use nutrient media that trigger the induction of spore formation.

The sporulation time is from 7 to 30 days depending on the microorganism used and on the nutrient medium used.

To inoculate the preculture- or production fermenters, the spores are either suspended with surface-active agents, for example a Tween80 (surfactant, available from Sigma-Aldrich Co., St. Louis, Mo. USA) solution, and transferred together with their nutrient medium into the fermenter or, if solid nutrient media are used, are washed off the solid nutrient substrates also using the said surface-active agents. The spore-containing solution obtained in this manner is then used to inoculate the fermenters. Preferably, both the recovery of the spores and the inoculation of the fermenters are carried out under sterile conditions.

To produce compounds of the formulae (III) within the scope of the present invention, bioreactors of various dimensions, embracing capacities of the order of from 0.001 $m^3$ to 450 $m^3$, may be used depending on the amount of product required.

If stirred vessel bioreactors are used, then the following fermentation parameters are to be considered as critical for the course of the reaction to be optimum:

1. Temperature: The biocatalytic oxidation reaction within the scope of the process according to the invention is preferably carried out in the mesophilic temperature range (temperature range of from 20° C. to 45° C.). The optimum temperature range for growth and product formation is from 20° C. to 32° C., especially from 24° C. to 30° C.

2. Aeration: The aeration rate is from 0.1 to 2.5 vvm (volume of air per volume of liquid per minute), preferably from 0.3 to 1.75 vvm. The aeration rate must, if necessary, be adapted to the acquired oxygen requirement in the course of the fermentation.

3. Pressure: Stirred vessel reactors are generally operated under slight excess pressure of from 02 to 1.0 bar, preferably from 0.5 to 0.7 bar, in order to reduce the risk of contamination.

4. pH value: The pH value may vary within certain limits depending on the microorganism used. If microorganisms from the Actinomycetes group are used, the initial pH value is from pH 6 to pH 8, preferably from pH 6.5 to pH 7.5.

If fungi are used, the initial pH of the culture solution is preferably from pH 4 to pH 8, especially from pH 6 to pH 7.5.

5. Stirring: The stirring speed depends on the type of stirrer used and the size of the fermenter. Within the scope of the present invention stirrers with impellers of the disc type are preferred which, with a stirred vessel reactor size of 0.002 $m^3$, are operated at speeds of from 150 rpm to 550 rpm, especially from 200 rpm to 500 rpm.

Within the scope of the present invention the duration of the fermentation varies from 20h to 10 days depending on the microorganism used. The biocatalytic reaction is discontinued when from about 25% to about 99.9%, more preferably from about 50% to about 99.9% and most preferably from about 80% to about 99.9% of the substrate (compounds of the formula (II)) added at the beginning has been converted into compounds of the formula (III).

To ascertain the optimum time for termination of the oxidation reaction, the course of the reaction is monitored for the whole of the fermentation by customary analysis processes, especially chromatographic processes, such as, for example, HPLC or thin layer chromatographic processes In a modification of the above outlined process, the bioreactor may only be used for generating biomass, which is then harvested by filtration or centrifugation. The biomass of the microorganism is then either immediately used as a biocatalyst for the conversion of compounds of formula (II) into compounds of formula (III) or stored in the cold either as such or after freeze drying or spray drying. Said microorganism, either freshly harvested or stored as described, is then further distributed to other vessels such as, for example, flasks preferably equipped with baffles or to stirred vessel bioreactors, wherein the bioconversion process is carried out. The substrate (compounds of the formula (II)) is added, whereby the microorganism and the substance to be oxidized can be brought into contact with one another in any manner. For practical reasons, a has proven advantageous to add the substrate, that is to say a compound of the formula (II), to the microorganism in a buffered solution which does not favor proliferation. The substrate (compounds of the formula (II)) to be oxidized can be used, for example, in powder form or in the form of a solution in either a suitable solvent such as those described herein previously.

In a preferred embodiment of the invention the substrate (compounds of the formula (II)) is first dissolved in a suitable solvent such as, for example, dimethyl sulfoxide or Tween40 (surfactant, available from Sigma-Aldrich Co., St. Louis, Mo. USA) or a combination of both, and added to baffled flasks containing a buffer solution, preferably phosphate buffer, more preferably a phosphate buffer of 0.07M pH 7.0. The resulting solution is then sterilized before the biocatalyst (biomass of the microorganism) is added. This reaction mixture is then incubated at room temperature and shaken at between 100 rpm and 150 rpm, preferably at about 120 rpm for about 2–7 days, depending on the microbial strain.

In a further preferred embodiment of the invention the substrate (compounds of the formula (II)) is first dissolved in a suitable solvent such as, for example, dimethyl sulfoxide or Tween40 (surfactant, available from Sigma-Aldrich Co., St. Louis, Mo. USA) or a combination of both, and added to baffled flasks containing a cultivation medium promoting growth of the microorganism to be used for carrying out the desired oxidation reaction. The resulting solution is then sterilized before the biocatalyst (biomass of the microorganism) is added. This reaction mixture is then incubated at room temperature and shaken at between 100 rpm and 150 rpm, preferably at about 120 rpm for about 2–9 days, depending on the microbial strain.

In a further specific embodiment of the invention a cell-free extract is prepared using wet cells, which are washed in a suitable buffer solution, resuspended in disruption buffer and disrupted by, for example, mechanical means at a temperature of between 2° C. and 15° C., preferably at a temperature of between 3° C. and 6° C. and most preferably at 4° C. The resulting suspension is centrifuged and the supernatant cell free extract is collected.

To the so obtained cell free extract solutions are added comprising a suitable aliquot of a foreign electron supply system such as, for example, ferredoxin and ferredoxin reductase and substrate. After the addition of substrate the mixture is preferably immediately and thoroughly mixed and aerated. Then a suitable aliquot of NADPH is added and the mixture incubated at a temperature of between 15° C. and 40° C., preferably at a temperature of between 20° C. and 35° C. and most preferably at 30° C.

Processing of the fermentation broth in order to recover the oxidation product (compounds of the formula (III)) can be carried out by processes customarily used in the art of fermentation (W. Crueger and A. Crueger, 1984; P. Präve, 1984).

First of all, the particulate constituents are removed from the reaction broth using filters, centrifuges or separators, to be extracted separately from the filtrate.

If vegetative or dead cells are used as biocatalyst, and if a portion of the reaction products (compounds of the formula (III) are present inside the cells, the cells must be disintegrated prior to extraction. For this purpose various cell disintegration methods are available based on mechanical, thermal, chemical or enzymatic processes.

Mechanical methods suitable for use in the process according to the invention are, for example, grinding in stirred ball mills or colloid mills, the use of pressure and relaxation in a homogenizer and cell disintegration by the action of ultrasound. Non-mechanical processes include cell disintegration by drying, lysis of the cells by osmotic shock, chemical autolysis and enzymatic lysis of the cells.

Once the particulate constituents have been removed, the reaction products are concentrated by extracting the culture solution and the separated cellular constituents with suitable solvents. For the extraction there are also numerous aids available that are customarily used in the art of fermentation, such as, for example, mixer-settlers, countercurrentcolumns, extraction centrifuges, among others.

It is also possible to concentrate the reaction products, for example, by membrane filtration, ultrafiltration, freeze concentration, ion exchange processes, among others.

The further processing of the crude product obtained after the extraction can be carried out by methods that are well established in microbiological and chemical research and in industrial use.

These processes include, for example, chromatographic methods,such as adsorption chromatography, ion exchange chromatography,molecular sieve chromatography, affinity chromatography, hydrophobic chromatography, partition chromatography, covalent chromatography and others, but in addition to these also various crystallisation processes.

Solvents suitable for extraction, either as such or as mixtures thereof are: aromatic hydrocarbons such as toluene, xylene mixtures or substituted naphthalenes, phthalates such as dibutyl phthalate or dioctyl phthalate, aliphatic hydrocarbons such as isomers of hexane, heptane, octane or paraffins or cyclohexane, alcohols and glycols and their ethers and esters, such as methanol, ethanol, 2-propanol, 1-butanol, tert.butanol, ethylene glycol, methyl tert.butyl ether, ethyl acetate, ethylene glycol monomethyl or monoethyl ether, ketones such as acetone or 2-butanone or cyclohexanone, chlorinated hydrocarbons such as dichloromethane or chloroform or carbon tetrachloride.

The term "surfactants" will also be understood to include mixtures of surfactants. Both water-soluble soaps and water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g., from coconut oil or tallow oil. Further suitable surfactants are also the fatty acid methyltaurin salts. More frequently, however, so-called synthetic surfactants are used, especially fatty sulphonates, fatty sulphates, sulphonated benz-imidazole derivatives or alkylarylsulphonates. The fatty sulphonates or sulphates are usually in the form of alkali metal salts, alkaline earth metal salts or unsubstituted or substituted ammonium salts and contain a $C_{10}$–$C_{22}$-alkyl radical which also includes the alkyl moiety of acyl radicals, e.g. the sodium or calcium salt of lignosulphonic acid, of dodecylsulphate, or of a mixture of fatty alcohol sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and form-aldehyde. Also suitable are corresponding phosphates, e.g. salts of the phosphoric acid ester of an adduct of p-nonylphenol with 4 to 14 moles of ethylene oxide; or phospholipids. The surfactants customarily employed in the art of formulation are described, inter alia, in the following publication: "1986 International McCutcheon's Emulsifiers and Detergents" The Manufacturing Confectioner Publishing Co., Glen Rock, N.J., U.S.A.

A preferred embodiment of the invention is a method to produce 4"-oxo-avermectin by bringing a biocatalyst such as a microorganism capable of converting avermectin to 4"-oxo-avermectin into contact with avermectin and isolating the produced 4"-oxo-avermectin from the reaction mixture.

An embodiment of the invention is a method to produce a compound of formula (III), which preferably is 4"-oxo-avermectin, which comprises the following steps (1) production of cells by inoculation of a nutrient media promoting cell growth with precultures of a microorganism capable of converting a compound of formula (II) to a compound of formula (III), preferably avermectin to 4"-oxo-avermectin;
(2) harvesting of the cells after growth
(3) dissolving a compound of formula (II), preferably avermectin, in an appropriate solvent
(4) addition of the solution from step (3) to a reaction medium which does not promote cell proliferation
(5) addition of cells from step (2) to the reaction medium from step (4)
(6) shaking or stirring of the reaction mixture of step (5) in the presence of air
(7) separation of the cells from the medium
(8) extraction of the supernatant and of the cells with appropriate solvents
(9) concentration of the organic solvent phases from step (8) in vacuo
(10) purification of a compound of formula (III), which preferably is 4"-oxo-avermectin, contained in the extract (9) by chromatography or crystallisation A further preferred embodiment of the invention is a method to produce a compound of formula (III), which preferably is 4"-oxo-avermectin, which comprises the following steps:

(1) production of cells by inoculation of a nutrient media promoting cell growth with precultures of a microorganism capable of converting a compound of formula (II) to a compound of formula (III), preferably avermectin to 4"-oxo-avermectin;
(2) harvesting of the cells after growth
(3) dissolving a compound of formula (II), preferably avermectin, in an appropriate solvent
(4) addition of the solution from step (3) to a reaction medium which does not promote cell proliferation
(5) addition of cells from step (2) to the reaction medium from step (4)
(6) shaking or stirring of the reaction mixture of step (5) in the presence of air
(7) whole broth extraction with an appropriate solvent
(8) phase separation
(9) concentration of the solvent phase from step (8) in vacuo
(10) purification of a compound of formula (III), which preferably is 4"-oxo-avermectin, contained in the extract (9) by chromatography or crystallisation A further preferred embodiment of the invention is a method to produce a compound of formula (III), which preferably is 4"-oxo-avermectin which comprises the following steps:

(1) dissolving a compound of formula (II), which preferably is avermectin, in an appropriate solvent
(2) addition of the solution from step (1) to a nutrient media promoting cell growth
(3) inoculation of the nutrient media of step (2) with precultures of a microorganism capable of converting a compound of formula (II) to a compound of formula (III), preferably avermectin to 4"-oxo-avermectin;
(4) cultivation of a microorganism capable of converting a compound of formula (II) to a compound of formula (III), preferably avermectin to 4"-oxo-avermectin;
(5) separation of the cells from the medium
(6) extraction of the supernatant and of the cells with appropriate solvents
(7) concentration of the organic solvent phases from step (6) in vacuo
(8) purification of a compound of formula (III), which preferably is 4"-oxo-avermectin, contained in the extract (7) by chromatography or crystallisation.

A further preferred embodiment of the invention is a method to produce a compound of formula (III), which preferably is 4"-oxo-avermectin, which comprises the following steps:

(1) dissolving a compound of formula (II), preferably avermectin, in an appropriate solvent
(2) addition of the solution from step (1) to a nutrient media promoting cell growth
(3) inoculation of the nutrient media of step (2) with precultures of a microorganism capable of converting avermectin to 4"-oxo-avermectin
(4) cultivation of a microorganism capable of converting a compound of formula (II) to a compound of formula (III), preferably avermectin to 4"-oxo-avermectin;
(5) whole broth extraction with an appropriate solvent
(6) phase separation
(7) concentration of the solvent phase from step (6) in vacuo
(8) purification of a compound of formula (III), which preferably is 4"-oxo-avermectin, contained in the extract (7) by chromatography or crystallisation In a second purely chemical step the so obtained compound of the formula (III) can be reacted with an amine of the formula $HN(R_8)R_9$, wherein $R_8$ and $R_9$ have the same meanings as given for formula (I), and which is known, in the presence of a reducing agent.

The reaction components can be reacted in the absence of a solvent, preferably however in the presence of a solvent. Another possibility consists in carrying out the reaction in an excess of one of the reaction partners, especially in a liquid amine. Usually the addition of an inert liquid solvent or diluent is however advantageous. Examples of such solvents or diluents are aromatic, aliphatic and alicyclic hydrocarbons and halogenated hydrocarbons, such as benzene, toluene, xylene, mesitylene, tetraline, chlorobenzene, dichlorbenzene, brombenzene, petrolether, hexane, cyclohexane, dichlormethane, trichlormethane, tetrachlormethane, dichlorethane, trichlorethene or tetrachlorethene; esters, such as acetic acid ethylester; ethers, such as diethylether, dipropylether, diisopropylether, dibutylether, tert.-butylmethylether, ethylenglycolemonomethylether, ethylenglycolemonoethylether, ethylenglycoledimethylether, dimethoxydiethylether, tetrahydrofurane or dioxane; ketones, such as acetone, methylethylketon or methylisobutylketon; alcohols, such as methanol, ethanol, propanol, isopropanol, butanol, ethylenglycol or glycerine; amides, such as N,N-dimethylformamide, N,N-diethylformamide, N,N-dimethylacetamide, N-methylpyrrolidone or hexamethyl phosphoric acid triamide; nitriles, such as acetonitrile or propionitrile; and sulfoxides, such as dimethylsulfoxide; organic acids, such as acetic acid; and water.

Preferred solvents are ethers such as tetrahydrofurane and ethylenglycoledimethylether, especially tetrahydrofurane; alcoholes such as methanol, ethanol or isopropanol; halogenated solvents such as dichloromethane or dichlorethane; aromatic solvents such as benzene or toluene; nitriles such as acetonitrile, amides such as N,N-dimethylformamide, carbonic acids such as acetic acid; water; and mixtures thereof.

Very especially preferred solvents are methanol or ethanol or mixtures thereof.

The reaction is preferrably carried out in a pH-range of between 0 and 14, especially between 2 and 10, in many cases between 6 and 9, very especially at pH 9.

The reaction is preferrably carried out in a temperature range of between −80° C. and +140° C., preferred between −30° C. and +100° C., in many cases between −10° C. and +80° C., especially between 0° C. and +50° C.

Preferred reducing agents are hydrides such as borohydrides; boranes; formic acid; formiates; or hydrogen. Especially preferred are hydrides such as sodiumborohydride, zincborohydride, lithiumborohydride, sodiumcyanoborohydride, sodiumtriacetoxyborohydride or tetramethyl-ammoniumtriacetoxyborohydride. Especially preferred is sodiumborohydride.

The reaction can be carried out—where applicable—in the presence of certain further chemicals such as a homogeneous or heterogeneous catalysts or acids. Especially suitable are acids such as hydrochloric acid, p-toluenesulfonic acid, acetic acid, propionic acid, tartaric acid or phthalic acid; Lewis acids such as for example titaniumtetrachloride, titaniumtetraisopropylate or zinc chloride; salts such as for example magnesiumperchlorate, sodiumacetate, sodium-potassiumtartrate, ytterbiumchloride or pyridinium-p-toluene-sulfonate; water absorbing agents such as for example sodiumsulfate, molecular sieve or silicagel; or mixtures thereof. Preferred additional agents are acids such as acetic acid, propionic add or tartaric acid; preferred is acetic acid. When the reduction is carried out with hydrogen, the addition of one or several suitable homogeneous or heterogeneous catalysts is advantageous. Preferred such catalysts are heterogeneous metal catalysts which are known in the art, preferrably Ni-, Pt- or Pd-catalysts, especially Raney-nickel and Lindlar catalyst (Pd—$CaCO_3$—PbO). Suitable homogeneous catalysts are especially Rhodium complexes such as Wilkinsons catalysts (Chloro-tris-triphenyl-rhodium).

The compounds of formula (I), in each case in free form or in salt form, may be in the form of one of the possible isomers or in the form of a mixture thereof, for example depending on the number of asymmetric carbon atoms in the molecule and the absolute and relative configuration thereof and/or depending on the configuration of non-aromatic double bonds in the molecule they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood hereinbefore and hereinafter, even if stereochemical details are not specifically mentioned in each case.

Mixtures of diastereoisomers and mixtures of racemates of compounds of formula (I), or salts thereof, obtainable in accordance with the process depending on the starting materials and procedures chosen or by other means, can be separated on the basis of the physicochemical differences between the constituents into the pure diastereoisomers or racemates in known manner, for example by fractional crystallisation, distillation and/or chromatography.

Mixtures of enantiomers, such as racemates, so obtainable can be resolved into the optical antipodes by known methods, for example by recrystallisation from an optically active solvent, by chromatography on chiral adsorbents, e.g. high-pressure liquid chromatography (HPLC) on acetyl cellulose, with the aid of suitable microorganisms, by cleavage with specific immobilised enzymes, via the formation of inclusion compounds, e.g. using chiral crown ethers, in which case only one enantiomer is complexed, or by conversion into diastereoisomeric salts, e.g. by reaction of a basic end product racemate with an optically active acid, such as a carboxylic acid, e.g. camphoric, tartaric or malic acid, or a sulfonic acid, e.g. camphorsulfonic acid, and separation of the resulting mixture of diastereoisomers, e.g. on the basis of their different solubilities by fractional crystallisation, into the diastereoisomers from which the desired enantiomer can be freed by the action of suitable, e.g. basic, agents.

Apart from by separation of corresponding mixtures of isomers, it is possible according to the invention to obtain pure diastereoisomers or enantiomers also by generally known methods of diastereoselective or enantioselective synthesis, for example by carrying out the process according to the invention using starting materials having a correspondingly suitable stereochemistry.

The compounds of formulae (I) and (III), acid addition products and the salts thereof can also be obtained in the form of their hydrates and/or can include other solvents, for example solvents which may have been used for the crystallisation of compounds occurring in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes or, especially, is formed under the reaction conditions.

Compounds of formula (I) and (III) obtainable in accordance with the process or by other means may be converted into different compounds of formula (I) and (III) in a manner known per se.

In the process of the present invention there are preferably used those starting materials and intermediates, in each case in free form or in salt form, which result in the compounds of formulae (I) and (III), or salts thereof, described at the beginning as being especially valuable.

In the case $R_9$ is hydrogen, the reaction step 2) may be split into two separate steps, wherein in a first step, a compound of the formula

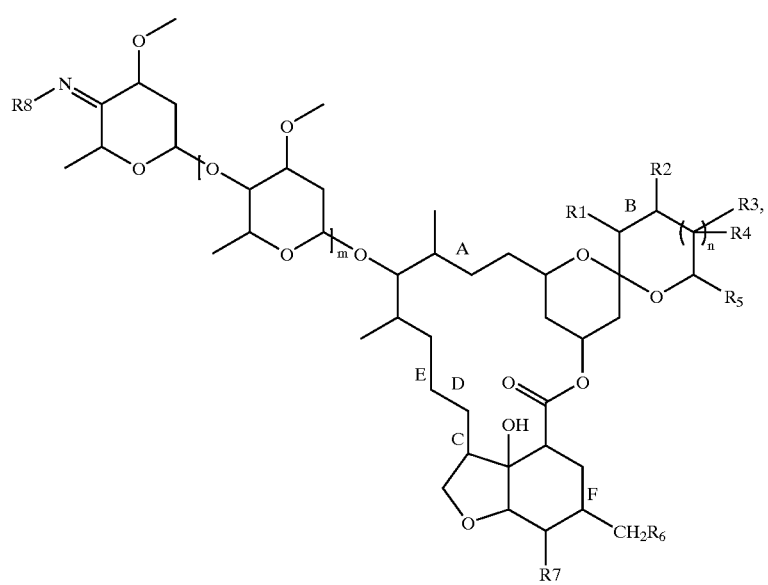

(IV)

in which $R_1$, $R_2$, $R_3$, $R_4$, $R_5$, $R_6$, $R_7$, $R_8$, m, n, A, B, C, D, E and F have the meanings given for formula (I) above, is formed by reaction of a compound of the formula (III) with a compound of the formula $H_2N(R_8)$, wherein $R_8$ has the same meanings as given for formula (I) above, and in a second step, the said compound of the formula (IV) is reduced according to the procedure of step 2) above. The said two individual steps may be carried out in a one pot synthesis without isolating the compound of the formula (IV); It may however be anevatageous to isolate the compound (IV), for instance for purification purposes. The compounds of the formula (IV) are novel and are also an aspect of the present invention.

EXAMPLES

The invention will be further described by reference to the following detailed examples. These examples are provided for purposes of illustration only, and are not intended to be limiting unless otherwise specified. The invention relates especially to the preparation processes described in the Examples.

Example 1

Cell Production 1.1 *Streptomyces tubercidicus* Strain I-1529

Precultures of strain I-1529 (*Streptomyces tubercidicus*; DSM-13135) are grown in 20 500 ml baffled Erlenmeyer flasks, each containing 100 ml of medium 2, with orbital shaking at 120 rpm at 28° C. for 3 days.

These cultures are used to inoculate a 50 liter fermenter containing 40 l medium 4. The cells were grown at 28° C. with an aeration of 0.7 vvm (=30 liter/min). The stirrer speed was maintained between 200 rpm and 300 rpm, guided by a $pO_2$-sensor, to prevent $pO_2$ falling below 25%. After 2 days of growth, the cells are harvested by centrifugation, using a flow-through centrifuge. 4.2 kg cells (wet) are obtained.

1.2 *Streptomyces tubercidicus* Strain R-922

*Streptomyces tubercidicus* Strain R-922 (DSM-13136) is grown in a Petri dish on ISP-2 agar (medium 5). This culture is used to inoculate 4 500 ml shake flasks with baffle, each containing 100 ml PHG medium (medium 6). These precultures are grown on an orbital shaker with 120 rpm at 28° C. for 96 h and then used to inoculate a 10 liter fermenter equipped with a mechanical stirrer and containing 8 liter PHG medium. This main culture is grown at 28° C. with stirring at 500 rpm and an aeration of 1.75 vvm (14 l/min) and a pressure of 0.7 bar. At the end of the exponential growth, after about 20 h, the cells are harvested by centrifugation. The yield of wet cells is 70–80 g/l culture. For further processing, the wet cells can be stored at 4° C., preferably not longer than a week.

Example 2

Reaction Procedure 2.1 Resting Culture 2.1.1 Reaction Conditions 35.5 g avermectin (techn.) are dissolved in 1.05 l dimethyl sulfoxide/Tween40 1:1. This solution is distributed by adding aliquots of 25 ml to 42 3 l-Erienmeyer flasks with baffle, each containing 1 l of reaction medium. These solutions are sterilized at 121° C. for 20 min. After cooling to room temperature, 100 g wet cells (fresh, or stored at 4° C. for not longer than 4 days), as prepared in Example 1.1 and 1.2, respectively, are added. Subsequently these reaction mixtures are shaken at room temperature with 120 rpm for 4–5 days.

Reaction Medium:
0.5 g molasses
0.5 g $MgCl_2$
12.5 mg $ZnCl_2$
12.5 mg $MnCl_2 \cdot 4H_2O$
25 mg $CoCl_2 \cdot 6H_2O$
12.5 mg $NiCl_2 \cdot 6H2O$ 2.5 mg $CuCl_2 \cdot 2H_2O$
6.3 mg $NaMoO_4 \cdot 2H_2O$
0.15 ml 1M HCl
adjust to 1 liter with phosphate buffer 70 mM pH 6.0, autoclave.

2.1.2 Work Up

The reaction mixtures are centrifuged in 500 ml polypropylene centrifuge flasks at 4° C. for 15 min at 13000×g.

The supernatants from the 40 l reaction mixture are pooled and extracted twice with methyl tert.butyl ether (0.5 vol. eq., 0.4 vol. eq.). The pooled methyl tert.butyl ether phases are then back-extracted three times with 0.185 vol. eq. distilled water. The methyl tert.butyl ether phase is concentrated in vacuo on the rotary evaporator. Drying of the residue yields 10–12 g extract S. The aqueous phases are discarded.

The centrifuged cells from 120 to 132 centrifuge flasks are extracted as follows:

Cells from 24 centrifuge flasks are transferred to a 2 l-Erlenmeyer flask. To each Erlenmeyer flask are added 80 g of diatomeous earth (Hyflo Supercell®, purified) and 1.2 l acetone. After manual mixing, the mixture is homogenized by means of a large magnetic stirbar. The resulting pulp is vacuum filtered through paper on a 20 cmØ Büchner funnel and washed with acetone until colorless elution. Thus filtrate C1 and filter cake C1 are obtained.

Filtrate C1 is concentrated in vacuo on a rotary evaporator to remove the acetone. The resulting aqueous phase is then extracted three times with 0.7 l toluene. The combined toluene phases are dried over anhydrous sodium sulfate. Filtration and evaporation on the rotary evaporator in vacuo yields extract C1.

Filter cake C1 is transferred to a 2 l-Erlenmeyer flask and manually mixed with 1.5 L toluene. The mixture is homogenized by means of a large magnetic stirbar. The resulting pulp is vacuum filtered through paper on a 20 cmØ Büchner funnel and washed with toluene until colorless elution. Thus filtrate C2 and filter cake C2 are obtained. Filter cake C2 is discarded.

Filtrate C2 is concentrated in vacuo on a rotary evaporator to yield extract C2 which is dried in high vacuum.

The combined extracts C1 and C2 from the 40 l reaction mixture are dried in high vacuum to yield 30–35 g extract C.

45 g of combined exacts S & C are flash chromatographed analogously to the description of Clark-Still et al. on a column packed with 1.5 kg silica gel (Merck 60, 0.040–0.063 mm) by elution with ethyl acetate:hexane 3:2 at 0.5 bar $N_2$-pressure and monitoring with thin layer chromatography. The yield of pure 4"-oxo-avermectin is 5.6 g.

2.1 Proliferating Culture

2.2.1 Reaction Conditions 1 g avermectin (techn.) is dissolved in 50 ml dimethyl sulfoxide/Tween40 1:1. This solution is distributed by adding aliquots of 2.5 ml to 20 500 ml-Erlenmeyer flasks with baffle, each containing 100 ml of medium 4. These solutions are sterilized at 121° C. for 20 min. After cooling to room temperature, 5 ml of preculture, as prepared in Example 1.1 and 1.2, respectively, are added. Subsequently these inoculated cultures were incubated at 28° C. for 7 days with orbital shaking at 120 RPM.

2.2.2 Work Up

The reaction mixtures are centrifuged in 500 ml polypropylene centrifuge flasks at 4° C. for 15 min at 13000×g and analogously processed as described in Example 3. 252 mg pure 4"-oxo-avermectin are obtained.

2.3 Cell-free Biocatalysis

2.3.1 Preparation of Cell Free Extract

Stock Solutions:
PP-buffer: 50 mM $K_2HPO_4/KH_2PO_4$ (pH 7.0)
Disruption buffer: 50 mM $K_2HPO_4/KH_2PO_4$ (pH 7.0).
  5 mM benzamidine,
  2 mM dithiothreitol,
  0.5 mM Pefabloc (from Roche Diagnostics)
Substrate: 10 mg avermectin are dissolved in 1 ml isopropanol.

6 g wet cells, washed in PP-buffer are resuspended in 35 ml disruption buffer and disrupted in a French press at 4° C. The resulting suspension is centrifuged for 1 h at 35000×g. The supernatant cell free extract is collected.

2.3.2 Development of an Assay for Enzyme Activity

Stock Solutions:
Ferredoxin solution 5 mg ferredoxin (from spinach) 1–3 mg/ml in Tris/HCl-buffer (from Fluka)
  or solution 5 mg ferredoxin (from *Clostridium pasteurianum*) 1–3 mg/ml in Tris/HCl-buffer (from Fluka)
  or solution 5 mg ferredoxin (from *Porphyra umbillicalis*) 1–3 mg/ml in Tris/HCl-buffer (from Fluka)
Ferredoxin Reductase: solution of 1 mg freeze dried ferredoxin reductase (from spinach) 3.9 U/mg in 1 ml $H_2O$ (from Sigma)
NADPH: 100 mM NADPH in $H_2O$ (from Roche Diagnostics)
(all stock solutions were stored at −20° C. and when in use they were kept on ice)

HPLC Conditions:
HPLC instrument: Merck-Hitachi
HPLC-column: 70×4 mm, Kromasil 100 C18, 3.5μ (from Macherey-Nagel, Switzerland)
solvent A: acetonitrile, containing 0.0075% trifluoroacetic acid
solvent B: water, containing 0.01% trifluoroacetic acid
flow: 1.5 ml/min
detection: UV 243 nm
sample: 30 μl
Retention times: avermectin B1a 3.18 min
  4Δ-oxo-avermectin B1a 4.74 min

| Pump table: | 0.0 min | 75% A | 25% B |
|---|---|---|---|
| linear gradient to | 7.0 min | 100% A | 0% B |
|  | 9.0 min | 100% A | 0% B |
| step to | 9.1 min | 75% A | 25% B |
|  | 12.0 min | 75% A | 25% B |

To 475 μl cell free extract the following solutions are added 10 μl ferredoxin, 10 μl ferredoxin reductase and 1 μl substrate. After the addition of substrate the mixture is immediately and thoroughly mixed and aerated. Then 5 μl of NADPH are added and the mixture incubated at 30° C. for 30 min. Then, 1 ml methyl-t-butyl ether is added to the reaction mixture and thoroughly mixed. The mixture is centrifuged for 2 min at 14000 rpm, and the methyl-t-butyl ether phase is transferred into a 10 ml flask and evaporated in vacuo by means of a rotary evaporator. The residue is dissolved in 200 μl acetonitrile and transferred into an HPLC-sample vial. Upon injection of a 30 μl sample a peak appeared at 4.74 min, indicating the presence of 4"-oxo-avermectin B1a. A mass of 870 Da can be assigned to this peak by HPLC-mass spectrometry which corresponds to the molecular weight of 4"-oxo-avermectin B1a.

When analyzing product formation by HPLC and HPLC-mass spectrometry, a second peak appears at 2.01 min corresponding to ketohydrate 4"-hydroxy-avermectin. This is an indication that the cell-free extract converts avermectin by hydroxylation to 4"-hydroxy-avermectin from which 4"-oxo-avermectin is formed by dehydration.

The spinach ferredoxin can be replaced by, for example, ferredoxin from the bacterium *Clostridium pasteurianum* or from the red alga *Porphyra umbilicalis*, which also result in the biocatalytic conversion of avermectin to 4"-oxo-avermectin.

Example 3

Steptomyces Strains

Strains of the genus Streptomyces that can be used in the process according to the invention and their relationship to *S tubercidicus* strains I-1529 and R-922 based on a 16s rDNA analysis can be seen from the following table.:

| Strain Number | Closest GenBank Match | % 16s rDNA Identity |
|---|---|---|
| I-1629 | *Streptomyces tubercidicus* DSM 40261 Type strain | 100 |
| R-922 | *Streptomyces tubercidicus* DSM 40261 Type strain | 100 |
| MAAG-7027 | *Streptomyces tubercidicus* DSM 40261 Type strain | 100 |
| DSM-40241 | (listed as *Streptomyces saraceticus* = ATCC-25496) | 100 |
| | *Streptomyces chattanoogensis* | 99.8 |
| | *Streptomyces lydicus ATCC 25470* = NRRL-2433 | |
| A/96-1208710 | *Streptomyces kasugaensis* DSM 40819 Type strain | 99.5 |
| | *Streptomyces kasugaensis* M338-M1 | 99.4 |
| NRRL-2433 | (listed as Type strain *Streptomyces lydicus* ssp *lydicus* = ATCC 25470 = CBS 703.69 = DSM 40461) | |

Example 4

Preparation of 4"-Deoxy-4"-epi-(methylamino)-avermectin B1 of the Formula 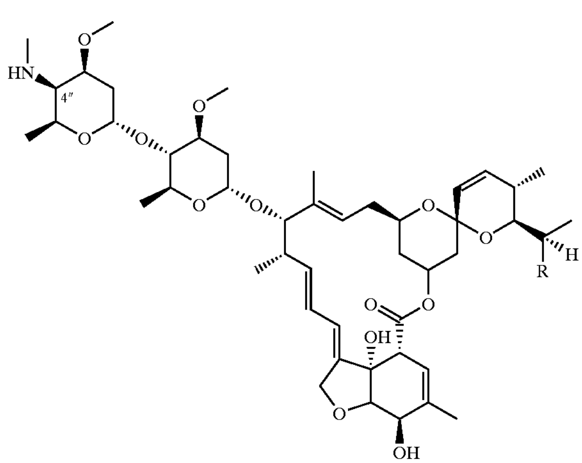 wherein R is methyl and ethyl;

3 ml acetic acid in 30 ml methanol are cooled to 0 to 5° C. Gaseous methylamine is added until the pH of the solution is 9.

To 8.25 ml of this solution of methylamine is added at 0° C. a solution of 1.0 g 4"-Oxo-avermectin B1 in 6 ml methanol. The mixture is allowed to warm up to ambient temperature and then stirred for a further 50 minutes at room temperature. Then, 90 mg sodiumborohydride in 2.5 ml ethanol are added and the resulting mixture stirred for another 45 minutes. 10 ml ethylacetate are added to the reaction mixture, the organic phase extracted three times with saturated aqueous sodiumhydrogencarbonate solution, the organic phase separated and dried over sodiumsulfate. The solvent is distilled off yielding 4"-Deoxy-4"-epi-(methylamino)-avermectin B1. The purity is over 90%.

Literature

Angelino S. A. G. F., Müller F., Plas H. C. van der (1985) Purification and immobilization of rabbit liver aldehyde oxidase. Biotechnol. Bioeng. 27: 447–455.

Bachmann S., Gebicka L., Gasyna Z., (1981) Immobilization of glucose isomerase on radiation-modified gelatine gel. Starch/Stärke 33: 63–66.

Barbaric S., Kozulic B., Leustek I., Pavlovic B., Cesi V., Mildner P. (1984) Crosslinking of glycoenzymes via their carbohydrate chains. In: 3rd Eur. Congr. Biotechnol., Vol. 1. Verlag Chemie, Weinheim, p. 307–312.

Beddows C. G., Guthrie J. T., Abdel-Hay F. I. (1981) The use of graft copolymers as enzyme supports immobilization of proteins and enzymes on a hydrolyzed nylon-coacrylonitrile system. Biotechnol. Bioeng. 23: 2885–2889.

Bettmann H., Rehm H. J. (1984) Degradation of phenol by polymer entrapped microorganisms. Appl. Microbiol. Biotechnol. 20: 285–290.

Bhairi S. M. (1997) A guide to the Properties and Uses of Detergents in Biology and Biochemistry, Calbiochem-Novabiochem Corp., San Diego Calif., 1997.

Bickerstaff G. F. (Ed.) (1997) Immobilisation of Enzymes and Cells (Methods in Biotechnology Series). Humana Press, Totowa N.J. USA, 1997.

Bihari V., Goswami P. P., Rizvi S. H. M., Kahn A. W., Basu S. K., Vora V. C. (1984) Studies on immobilized fungal spores of microbial transformation of steroids: IIa-hydroxylation of progesterone with immobilized spores of *Aspergillus ochraceus* G8 on polyacrylamide gel and other matrices. Biotechnol. Bioeng. 26: 1403–1408.

Black G. M., Webb C., Matthews T. M., Atkinson B. (1984) Practical reactor systems for yeast cell immobilization using biomass support particles. Biotechnol. Bioeng. 26: 134–141.

Cabral J. M. S., Novais J. M., Cardoso J. P. (1984) Coupling of glucoamylase on alkylamine derivative of titanium(IV) activated controlled pore glass with tannic acid. Biotechnol. Bioeng. 26: 386–388.

Cannon J. J., Chen L.-F., Flickinger M. C., Tsao G. T. (1984) The development of an immobilized lactate oxidase system for lactic acid analysis. Biotechnol. Bioeng. 26: 167–173.

Cantarella M., Migliaresi C., Tafuri M. G., Afani F. (1984) Immobilization of yeast cells in hydroxymethacrylate gels. Appl. Microbiol. Biotechnol. 20: 233–237.

Chipley J. R. (1974) Effects of 2,4-dinitrophenol and N,N'-dicyclo-hexylcarbodiimide on cell envelope-associated enzymes of *Escherichia coli* and *Salmonella enteritidis*. Microbios. 10: 115–120.

Clark-Still W., Kahn M., Mitra A. (1978) Rapid chromatographic technique for preparative separations with moderate resolution. J. Org. Chem. 43: 2923–2925.

Crueger W., Crueger A. (1984) Biotechnologie-Lehrbuch der angewandten Mikrobiologie, 2nd edition, R. Oldenbourg Vedag Munich, Vienna, 1984.

Dennis, K. E.; Clark, D. S.; Bailey, J. E.; Cho, Y. K.; Park, Y. H. (1984) Immobilization of enzymes in porous supports: Biotechnol. Bioeng. 26: 892–900.

Deo Y. M., Gaucher G. M. (1984) Semicontinuous and continuous production of penicillin-G by *Penicillium chrysogenum* cells immobilized in k-carrageenan beads. Biotechnol. Bioeng. 26: 285–295.

De Rosa M., Gambacorta A., Lama L., Nicolaus B. (1981) Immobilization of thermophilic microbial cells in crude egg white. Biotechnol. Lett 3: 183–188.

DiLuccio R. C., Kirwan D. J. (1984) Effect of dissolved oxygen on nitrogen fixation by A. Vinelandii. II. Ionically adsorbed cells. Biotechnol. Bioeng. 26: 87–91.

Erhardt H. M., Rehm H. J. (1985) Phenol degradation by microorganisms adsorbed on activated carbon. Appl. Microbiol. Biotechnol. 21: 32–36.

Eikmeier H., Rehm H. J. (1984) Production of citric acid with immobilized *Aspergillus niger*. Appl. Microbiol. Biotechnol. 20: 365–370.

Förberg C., Häggström L. (1984) Adsorbed cell systems controlled by the nutrient dosing technique. In: 3rd Eur. Congr. Biotechnol. Vol. 2. Verlag Chemie, Weinheim, p. 115–120.

Gainer J. L., Kirwan D. J., Foster J. A., Seylan E. (1980) Use of adsorbed and covalently bound microbes in reactors. Biotechnol. Bioeng. Symp. 10: 35–42.

Giard D. J., Loeb D. H., Thilly W. G., Wang D. I. C., Levine D. W. (1979) Human interferon production with diploid fibroblast cells grown on microcarriers. Biotechnol. Bioeng. 21: 433–442.

Greene Th. W., Wuts P. G. M. (1999) Protective Groups in Organic Synthesis, 3rd edition, John Wiley & Sons, New York N.Y. 1999.

Hartmeier W. (1986), Immobilisierte Biokatalysatoren, Springer Verlag, Berlin, Heidelberg, New York, Tokyo, 1986.

Hofstee B. H. J. (1973) Immobilization of enzymes through non-covalent binding to substituted agaroses. Biochem. Biophys. Res. Commun. 53:1137–1144.

Ibrahim M., Hubert P., Dellacherie E., Magadalou J., Muller J., Siest G. (1985) Covalent attachment of epoxide hydrolase to dextran. Enz. Microbiol. Technol. 7: 66–72.

Jack T. R., Zajic J. E. (1977) The enzymatic conversion of L-histidine to urocanic acid by whole cells of *Micrococcus luteus* immobilized on carbodiimide activated carboxymethylcellulose. Biotechnol. Bioeng. 19: 631.

Jirku V., Turkova J., Krumphanzl V. (1980) Immobilization of yeast with retention of cell division and extracellular production of macromolecules. Biotechnol. Lett. 2: 509–513.

Karube, I.; Kawarai, M.; Matsuoka, H.; Suzuki, S. (1985) Production of L-glutamate by immobilized protoplasts. Appl. Microbiol. Biotechnol. 21: 270–272.

Kato T., Horikoshi K. (1984) Immobilized cyclomaltodextrin glucano-transferase of an alkalophilic Bacillus sp. no 38-2. Biotechnol. Bioeng. 26: 595–598.

Kaul R., D'Souza S. F., Nadkami G. B. (1984) Hydrolysis of milk lactose by immobilized (-galactosidase-hen egg white powder. Biotechnol. Bioeng. 26: 901–904.

Khan S. S., Siddiqi A. M. (1985) Studies on chemically aggregated pepsin using glutaradehyde. Biotechnol. Bioeng. 27: 415–419.

Krakowiak W., Jach M., Korona J., Sugier H. (1984) Immobilization of glucoamylase on activated aluminium oxide. Starch/Stärke 36: 396–398.

Kühn W., Kirstein D., Mohr P. (1980) Darstellung und Eigenschaften trägerfixierter Glukoseoxydase. Acta Biol. med. Germ. 39:1121–1128.

Mazumder T. K., Sonomoto K., Tanaka A., Fukui S. (1985) Sequential conversion of cortexolone to prednisolone by immobilized mycelia of *Curvularia lunata* and immobilized cells of Arthrobacter simplex. App. Microbial. Biotechnol. 21: 154–161.

Messing R. A., Oppermann R. A. (1979) Pore dimensions for accumulating biomass. I. Microbes that reproduce by fission or budding. Biotechnol. Bioeng. 21: 49–58.

Miyawaki O., Wingard jr L. B. (1984) Electrochemical and enzymatic activity of flavin dinucleotide and glucose oxidase immobilized by adsorption on carbon. Biotechnol. Bioeng. 26: 658–694.

Monsan P., Combes D., Alemzadeh I. (1984) Invertase covalent grafting onto corn stover. Biotechnol. Bioeng. 26: 658–664.

Mori T., Sato T., Tosa T., Chibata I. (1972) Studies on immobilised enzymes. X. Preparation and properties of aminoacylase entrapped into acrylamide gel-lattice. Enzymologia 43: 213–226.

Nakajima H., Sonomoto K., Usui N., Sato F., Yamada Y., Tanaka A., Fukui S., (1985) Entrapment of Lavendula Vera and production of pigments by entrapped cells. J. Biotechnol. 2:107–117.

Navarro J. M., Durand G. (1977) Modification of yeast metabolism by immobilization onto porous glass. Eur. J. Appl. Microbiol. Biotechnol. 4: 243–254.

Präve P., Faust U., Sittig W., Sukatsch. D. A. (1984) Handbuch Biotechnologie, 2nd edition, R. Oldenbourg Verlag Munich, Vienna, 1984.

Qureshi N., Tamhane D. V. (1985) Production of mead by immobilized whole cells of *Saccharomyces cerevisiae*. Appl. Microbiol. Biotechnol. 21: 280–281.

Raghunath K., Rao K. P., Joseph U. T. (1984) Preparation and characterization of urease immobilized onto collagen-poly(glycidyl methacrylate) graft copolymer. Biotechnol. Bioeng. 26: 104–109.

Romanovskaya V. A., Karpenko V. I., Pantskhava E. S., Greenberg T. A., Malashenko Y. R. (1981) Catalytic properties of immobilized cells of methane-oxidizing and methanogenic bacteria. In: Moo-Young M (Ed.) Advances in Biotechnology, Vol. 3 Pergamon, Toronto, p. 367–372.

Shimizu S., Morioka H., Tani Y., Ogata K. (1975) Synthesis of coenzyme A by immobilized microbial cells. J. Ferm. Technol. 53: 77–83.

Talsky G., Gianitsopoulos G. (1984) Intermolecular crosslnking of enzymes. In: 3rd Eur. Congr. Biotechnol., Vol. 1 Verlag Chemie, Weinheim, p. 299–305.

Umemura I., Takamatsu S., Sato T., Tosa T., Chibata I. (1984) Improvement of production of L-aspartic acid using immobilized microbial cells. Appl. Microbiol. Biotechnol. 20:.291–295.

Van Haecht J. L., Bolipombo M., Rouxhet P. G. (1985) Immobilization of *Saccharomyces cerevisiae* by adhesion: treatment of the cells by Al ions. Biotechnol. Bioeng. 27: 217–224.

Vogel H. J., Brodelius P. (1984) an in vivo 31P NMR comparison of freely suspended and immobilized *Catharanthus roseus* plant cells. J. Biotechnol. 1: 159–170.

Weetail H. H., Mason R. D. (1973) Studies on immobilized papain. Biotechnol. Bioeng. 15: 455–466.

Wiegel J., Dykstra M. (1984) *Clostridium thermocellum*: adhesion and sporulation while adhered to cellulose and hemicellulose. Appl. Microbiol. Biotechnol. 20: 59–65.

Workman W. E., Day D. F. (1984) Enzymatic hydrolysis of insulin to fructose by glutaraldehyde fixed yeast cells. Biotechnol. Bioeng. 26: 905–910.

What is claimed is:

1. A process for the preparation of a compound of the formula

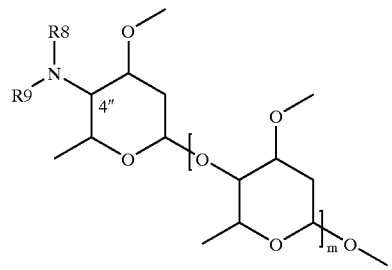
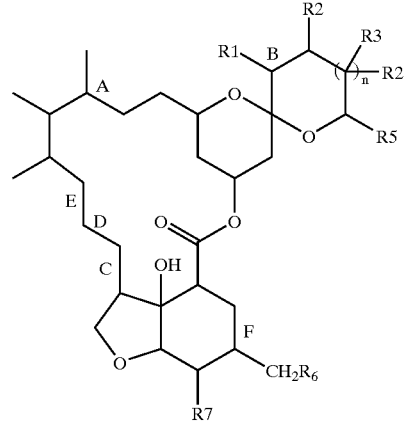

(I)

in which $R_1$–$R_9$, represent, independently of each other hydrogen or a substituent;

m is 0, 1 or 2;

n is 0, 1, 2 or 3; and the bonds marked with A, B, C, D, E and F indicate, independently of each other, that two adjacent carbon atoms are connected by a double bond, a single bond, a single bond and a epoxide bridge of the formula

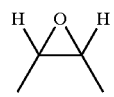

or a single bond and a methylene bridge of the formula

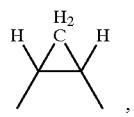, including, where applicable, an E/Z isomer, a mixture of E/Z isomers, and/or a tautomer thereof, in each case in free form or in salt form, which process comprises
1) bringing a compound of the formula

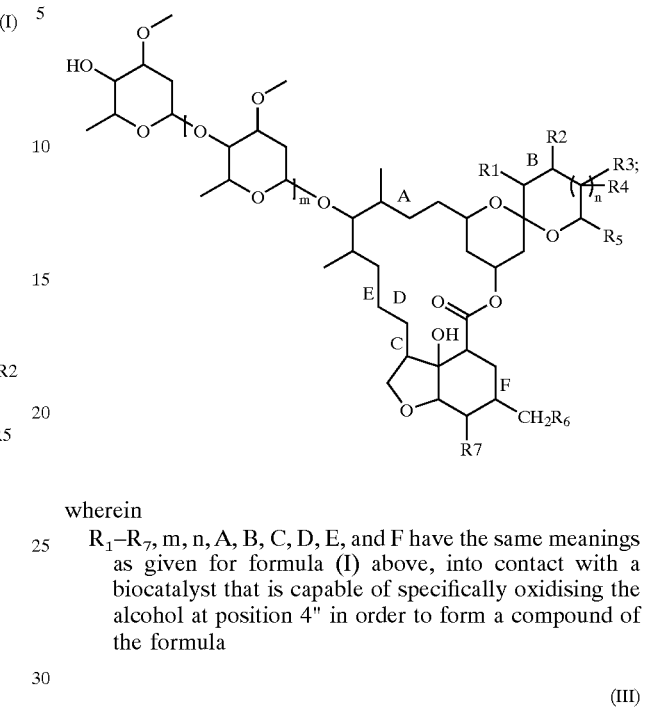

(II)

wherein
$R_1$–$R_7$, m, n, A, B, C, D, E, and F have the same meanings as given for formula (I) above, into contact with a biocatalyst that is capable of specifically oxidising the alcohol at position 4″ in order to form a compound of the formula

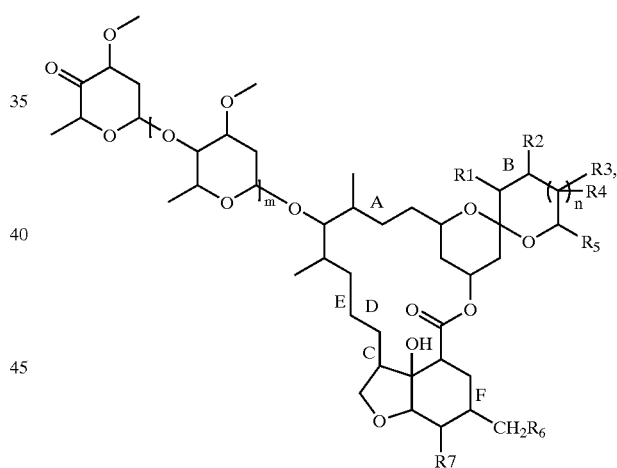

(III)

in which $R_1$, $R_2$, $R_3$, $R_4$, $R_5$, $R_6$, $R_7$, m, n, A, B, C, D, E and F have the meanings given for formula (I); and
2) reacting the compound of the formula (III) with an amine of the formula HN($R_8$)$R_9$, wherein $R_8$ and $R_9$ have the same meanings as given for formula (I), and which is known, in the presence of a reducing agent; and, in each case, if desired, converting a compound of formula (I) obtainable in accordance with the process or by another method, or an E/Z isomer or tautomer thereof, in each case in free form or in salt form, into a different compound of formula (I) or an E/Z isomer or tautomer thereof, in each case in free form or in salt form, separating a mixture of E/Z isomers obtainable in accordance with the process and isolating the desired isomer, and/or converting a free compound of formula (I) obtainable in accordance with the process or by another method, or an E/Z isomer or tautomer thereof, into a salt or converting a salt, obtainable in accordance with the process or by another method, of a compound of formula (I) or of an E/Z isomer or tautomer thereof into the free compound of formula (I) or an E/Z isomer or tautomer thereof or into a different salt.

2. A process for the preparation of a compound of the formula (III)

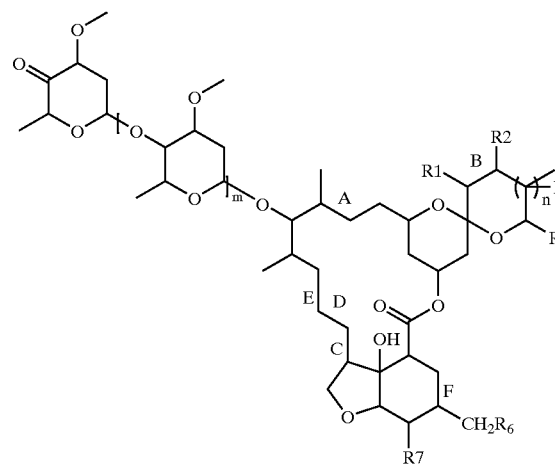

in which $R_1$–$R_7$ represent, independently of each other, hydrogen or a substituent;

m is 0, 1 or 2;

n is 0, 1, 2 or 3; and the bonds marked with A, B, C, D, E and F indicate, independently of each other, that two adjacent carbon atoms are connected by a double bond, a single bond, a single bond and a epoxide bridge of the formula

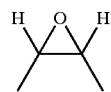

or a single bond and a methylene bridge of the formula

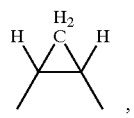, including, where applicable, an E/Z isomer, a mixture of E/Z isomers, and/or a tautomer thereof, in each case in free form or in salt form, which process comprises 1) bringing a compound of the formula (II)

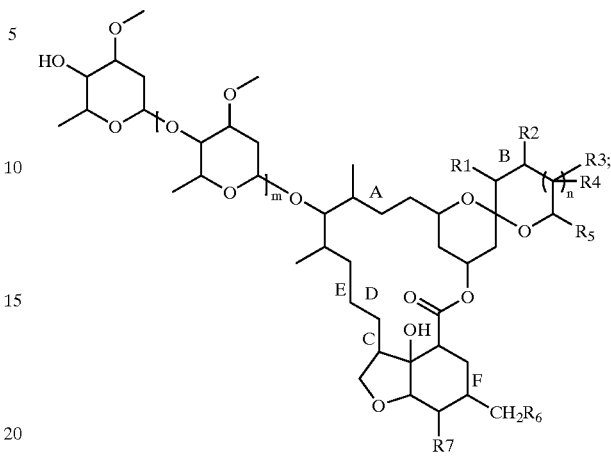

wherein $R_1$–$R_7$, m, n, A, B, C, D, E and F have the same meanings as given for formula (III) above, into contact with a biocatalyst that is capable of specifically oxidising the alcohol at position 4", maintaining said contact for a time sufficient for the oxidation reaction to occur and isolating and purifying the compound of formula (III).

3. A process according to claim 1 for the preparation of a compound of the formula (I), in which n is 1;

m is 1;

A is a double bond;

B is single bond or a double bond,

C is a double bond,

D is a single bond,

E is a double bond,

F is a double bond; or a single bond and a epoxy bridge; or a single bond and a methylene bridge;

$R_1$, $R_2$ and $R_3$ are H;

$R_4$ is methyl;

$R_5$ is $C_1$–$C_{10}$-alkyl, $C_3$–$C_8$-cycloalkyl or $C_2$–$C_{10}$-alkenyl;

$R_6$ is H;

$R_7$ is OH;

$R_8$ and $R_9$ are independently of each other H; $C_1$–$C_{10}$-alkyl or $C_1$–$C_{10}$-acyl; or together form —$(CH_2)_q$—; and q is 4, 5 or 6.

4. A process according to claim 1 for the preparation of a compound of the formula (I), in which n is 1;

m is 1;

A, B, C, E and F are double bonds;

D is a single bond;

$R_1$, $R_2$, and $R_3$ are H;

$R_4$ is methyl;

$R_5$ is s-butyl or isopropyl;

$R_6$ is H;

$R_7$ is OH;

$R_8$ is methyl $R_9$ is H.

5. A process according to claim 1 for the preparation of 4"-deoxy-4"-N-methylamino avermectin $B_{1a}/B_{1b}$ benzoate salt.

6. A process according to claim 1 or 2, wherein the biocatalyst is a microorganism.

7. A process according to claim 1 or 2, wherein the biocatalyst is selected from the group consisting of
   a) a living microorganism in the form of vegetative cells, resting cells or freeze dried cells,
   b) a dead microorganism, preferably in a partially disintegrated form, with the cell wall/cell membrane mechanically or chemically or by spray drying permeabilized,
   c) crude extracts of the cell contents of the said microorganism, and
   d) an enzyme that converts the compounds of the formula (II) into compounds of formula (III), and
   e) the spores of said microorganism of (a).

8. A process according to claim 3 or 4, wherein the microorganism is a representative of the genus Streptomyces.

9. A process according to claim 8, wherein the microorganism is a Streptomyces strain selected from the group consisting of *Streptomyces tubercidicus; Streptomyces chattanoogensis, Streptomyces lydicus, Streptomyces saraceticus* and *Streptomyces kasugaensis.*

10. A process according to claim 9 wherein the microorganism is the strain Streptomyces R-922 deposited under accession number DSM-13136.

11. A process according to claim 9 wherein the microorganism is the strain Streptomyces R-1529 deposited under accession number DSM-13135.

12. A process to produce a compound of formula (III) which comprises the following steps:
    (1) production of cells by inoculation of a nutrient media promoting cell growth with precultures of a microorganism capable of converting a compound of formula (II) to a compound of formula (III);
    (2) harvesting of the cells after growth;
    (3) dissolving a compound of formula (II), in an appropriate solvent;
    (4) addition of the solution from step (3) to a reaction medium which does not promote cell proliferation;
    (5) addition of cells from step (2) to the reaction medium from step (4);
    (6) shaking or stirring of the reaction mixture of step (5) in the presence of air;
    (7) separation of the cells from the medium;
    (8) extraction of the supernatant and of the cells with appropriate solvents;
    (9) concentration of the organic solvent phases from step (8); and
    (10) purification of a compound of formula (III) contained in the extract (9) by chromatography or crystallisation.

13. A process to produce a compound of formula (III) which comprises the following steps:
    (1) dissolving a compound of formula (II) in an appropriate solvent;
    (2) addition of the solution from step (1) to a nutrient media promoting cell growth;
    (3) inoculation of the nutrient media of step (2) with precultures of a microorganism capable of converting a compound of formula (II) to a compound of formula (III);
    (4) cultivation of a microorganism capable of converting a compound of formula (II) to a compound of formula (III);
    (5) separation of the cells from the medium;
    (6) extraction of the supernatant and of the cells with appropriate solvents;
    (7) concentration of the organic solvent phases from step (6) in vacuo; and
    (8) purification of a compound of formula (III) contained in the extract (7) by chromatography or crystallisation.

14. A process according to claims 12 or 13, wherein the compound of formula (II) is avermectin and the compound of formula (III) is 4"-oxo-avermectin.

* * * * *